US012673107B2

(12) United States Patent
Crombet Ramos et al.

(10) Patent No.: US 12,673,107 B2
(45) Date of Patent: Jul. 7, 2026

(54) USE OF THERAPEUTIC COMPOSITIONS FOR THE TREATMENT OF PATIENTS WITH TUMORS OF EPITHELIAL ORIGIN

(71) Applicants:Centro de Inmunología Molecular, Havana (CU); Innovative Immunotherapy Alliance, S.A., Mariel (CU)

(72) Inventors: Tania Crombet Ramos, Havana (CU); Circe Mesa Pardillo, Havana (CU); Kalet León Monzón, Havana (CU); Zaima Mazorra Herrera, Havana (CU); Danay Saavedra Hernández, Havana (CU); Patricia Lorenzo-Luaces Álvarez, Havana (CU); Grace Dy, Buffalo, NY (US); Mary Reid, Buffalo, NY (US); Rachel Evans, Buffalo, NY (US); Jason Muhitch, Buffalo, NY (US); Kelvin Lee, Buffalo, NY (US); Alan Hutson, Buffalo, NY (US); Candace Johnson, Buffalo, NY (US)

(73) Assignees: Innovative Immunotherapy Alliance S.A., Artemisa (CU); Centro de Inmunología Molecular, Havana (CU)

( * ) Notice: Subject to any disclaimer, the term of this patent is extended or adjusted under 35 U.S.C. 154(b) by 0 days.

(21) Appl. No.: 17/789,888

(22) PCT Filed: May 19, 2022

(86) PCT No.: PCT/CU2022/050004
§ 371 (c)(1),
(2) Date: Jun. 29, 2022

(87) PCT Pub. No.: WO2022/247972
PCT Pub. Date: Dec. 1, 2022

(65) Prior Publication Data
US 2024/0173392 A1 May 30, 2024

(30) Foreign Application Priority Data
May 26, 2021 (CU) .................................. 2021-0045

(51) Int. Cl.
*A61K 47/62* (2017.01)
*A61K 39/00* (2006.01)
*A61K 39/395* (2006.01)

(52) U.S. Cl.
CPC ...... *A61K 47/62* (2017.08); *A61K 39/001104* (2018.08); *A61K 39/395* (2013.01); *A61K 2039/505* (2013.01); *A61K 2039/6068* (2013.01)

(58) Field of Classification Search
CPC ...................................................... A61K 47/62
USPC ...................................................... 424/142.1
See application file for complete search history.

(56) References Cited

FOREIGN PATENT DOCUMENTS

WO WO 2004/058157 A2 * 7/2004

OTHER PUBLICATIONS

Kulemann et al (Nature Scientific Reports, 2017, 4510, 11 pages).*
Saavedra et al (Frontiers in Immunology, 2017, vol. 8, Article 269, 7 pages).*
Jeanson et al (Journal of Thoracic Oncology, 2019, 14(6): 1095-1101).*
Wu et al (International Immunopharmacology, 2020, 85, 106613, 10 pages).*
Tockman et al (Cancer Res., 1992, 52:2711s-2718s).*
Doroshow et al (Clinical Cancer Research, 2019, 25(15): 4592-4602).*
Raponi et al (Current Opinion in Pharmacology, 2008, 8: 413-418).*
Nelson et al (Journal of the National Cancer Institute, 1999, 91(23): 2032-2038).*
Dy G. et al: "P2.04-26 Interim Results from a Phase I/II Trial of Nivolumab in Combination with CIMAvax-EGF as Second-Line Therapy in Advanced NSCLC", Journal of Thoracic Oncology, vol. 13, No. 10, p. S740 (2018).
International Search Report and Written Opinion for Application No. PCT/CU2022/050004 dated Nov. 11, 2022.
Kaur Jasmine et al: "Immunotherapy for non-small cell lung cancer (NSCLC), as a stand-alone and in combination therapy", Critical Reviews in Oncology/Hematology, vol. 164, (2021).
Nct02955290: "CIMAvax Vaccine, Nivolumab, and Pembrolizumab in Treating Patients With Advanced Non-small Cell Lung Cancer or Squamous Head and Neck Cancer—Full Text View—ClinicalTrials. gov", Aug. 15, 2022 (Aug. 15, 2022), XP055953674, Retrieved from the Internet: URL:https://clinicaltrials.gov/ct2/show/NCT02955290.
Neninger E. et al: "P2.01-92 Cimavax-EGF in Combination with First-Line Chemotherapy in III Stage NSCLC", Journal of Thoracic Oncology, vol. 14, No. 10, pp. S676-S677 (2019).

(Continued)

*Primary Examiner* — Sean E Aeder
(74) *Attorney, Agent, or Firm* — Foley Hoag LLP; Philip S. Choi; Erin M. Foley

(57) ABSTRACT

The present invention relates to the branches of Biotechnology and Medicine. It describes the use of therapeutic compositions comprising a compound that blocks epidermal growth factor and an antibody that blocks the PD-1/PD-1 ligand signaling pathway in the treatment of tumors of epithelial origin, particularly those that express the native form for human KRAS protein. In patients with cancer of epithelial origin expressing native KRAS treated with said therapeutic compositions, an increase in their survival was observed.

20 Claims, 2 Drawing Sheets

Specification includes a Sequence Listing.

(56)             References Cited

OTHER PUBLICATIONS

Passiglia Francesco et al: "Efficacy of nivolumab in pre-treated non-small-cell lung cancer patients harbouringmutations", British Journal of Cancer, vol. 120, No. 1, pp. 57-62 (2018).
Rodriguez Pedro et al: "A Phase III 1-11 Clinical Trial of the Epidermal Growth Factor Vaccine CIMAvax-EGF as Switch Maintenance Therapy in Advanced Non-Small Cell Lung Cancer Patients", Clinical Cancer Research, vol. 22, No. 15, Aug. 1, 2016 (Aug. 1, 2016), pp. 3782-3790.

* cited by examiner

Days

Days

Time (months)

Time (months)

SEQUENCE LISTING

<160> NUMBER OF SEQ ID NOS: 2

<210> SEQ ID NO 1
<211> LENGTH: 189
<212> TYPE: PRT
<213> ORGANISM: Homo sapiens -continued

<400> SEQUENCE: 1

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 2
<211> LENGTH: 187
<212> TYPE: PRT
<213> ORGANISM: Homo sapiens

<400> SEQUENCE: 2

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Arg
145                 150                 155                 160

Glu Ile Arg Lys His Lys Glu Lys Met Ser Lys Asp Gly Lys Lys Lys
                165                 170                 175
```

-continued

```
Lys Lys Lys Ser Lys Thr Lys Cys Val Ile Met
            180                     185
```

USE OF THERAPEUTIC COMPOSITIONS FOR THE TREATMENT OF PATIENTS WITH TUMORS OF EPITHELIAL ORIGIN

CROSS-REFERENCE TO RELATED APPLICATIONS

This application is the U.S. national phase of International Patent Application No. PCT/CU2022/050004, filed on 19 May 2022, which claims the benefit of priority to Cuban Patent Application Serial No. 2021-0045, filed on 26 May 2021; the entire contents of each of said applications are incorporated herein in their entirety by this reference.

SCOPE OF THE TECHNIQUE

The present invention relates to the branches of Biotechnology and Medicine. In particular described, the use of therapeutic compositions for the treatment of patients with tumors of epithelial origin by simultaneous blocking of the epidermal growth factor and the signaling pathway for PD1/PD1 ligand.

BACKGROUND

Molecules called "checkpoints", among which the PD1 receptor and its PDL1 ligand stand out, negatively regulate the antitumor response generated by the immune system. Monoclonal antibodies (mAbs) that block the transmission of the inhibitory signal at these checkpoints (anti-CPI) induce a more efficient antitumor response. As of December 2020, seven anti-CPI mAbs had been approved for the treatment of numerous "immunosensitive" malignant tumors, such as melanoma, lung cancer, squamous head and neck tumors, hepatocarcinoma, urothelial cancer, gastric cancer, breast and colorectal tumors (Ravindranathan D et al. (2021) Biology, 10: 325).

Among the most successful anti-CPI mAbs are PD1-specific (anti-PD1) Nivolumab and Pembrolizumab and Atezolizumab and Durvalumab against PDL1. These therapies have been shown to be more effective in those tumors that express PDL1 molecules and have a high frequency of mutations and an infiltrate of immune cells potentially capable of attacking the tumor if the inhibitory signal is blocked (Gibney G T y cols. (2016) Lancet Oncol. 17(12): e542-e551). Low molecular weight inhibitors have also been developed against PD1/PDL1 with encouraging results in terms of blocking this signaling pathway without showing adverse effects related to the immune system (Liu Ch y cols. (2021) Cancer Cell Int. 21:e1-e17).

The epidermal growth factor receptor (EGFR) is a tyrosine kinase receptor and known oncogene (Yarden Y. (2001) European Journal of Cancer. 37: S3-S8), which is activated by seven natural ligands. Several studies have reported differential activation of the EGFR signaling cascade, depending on the ligand that binds to EGFR. Ligands such as EGF induce signaling that favors tumor proliferation while low-affinity ligands such as ampfiregulin promote differentiation (Freed D M y cols. (2017) Cell 171: 1-13). Differential activation of the ligand-dependent signaling cascade may be crucial in targeting therapies toward these molecules in contrast to the direct receptor blockade, for example, with anti-EGFR mAbs or inhibitors of the TKI signaling cascade. Such differences may influence the tolerability/safety of treatments, as well as greater or lesser clinical efficacy in different therapeutic contexts. In this sense, a therapeutic modality that targets EGFR ligands is the use of vaccine compositions that induce specific antibodies (Abs) against a ligand and consequently blocking its interaction with EGFR. An example of this therapeutic strategy is the CIMAvax-EGF vaccine that generates specific mAbs against human epidermal growth factor (EGF), depriving the tumor of this important ligand. Numerous clinical trials in patients with non-small cell lung cancer (NSCLC) immunized with CIMAvax-EGF have shown that the vaccine is safe and immunogenic. From the point of view of clinical response, administration of the vaccine has significantly increased patient survival (Rodriguez P C y cols. (2016) Clin Cancer Res. 22(15):3782-90).

One of the most important molecules involved in EGFR signaling is the GTPase KRAS. This molecule also activates multiple signaling cascades involved in tumorigenesis. Approximately 30% of all human tumors have mutations in the gene that codes for KRAS, which induces some constitutive activation of the EGF-R cascade independently of conventional membrane receptor activation (Fernández-Medarde, A y cols. (2011) Genes and Cancer. 2: 344-358).

The mutations in this gene predominates in some of these neoplasias, such as pancreatic adenocarcinoma, showing mutations in 90% of tumors. In other adenocarcinomas such as colon, it is present in 40% of them. In the case of the lung, the KRAS mutation is present in 30% of all non-small cell lung tumors, mainly in adenocarcinoma histology (Moore A R y cols. (2020) Nat Rev Drug Discov. 19(8): 533-552).

In tumors such as the pancreas and colon, the presence of KRAS mutations favors tumor growth and resistance to therapies (Haigis K M et al. (2008) Nat Genet. 40: 600-8.; Bournet B et al. (2016) Clin Transl Gastroenterol. 7: e157). However, in others, such as lung adenocarcinomas, there are controversial data on the prognostic value of mutations in this gene (Shepherd F A et al. (2013) J Clin. Oncol. 31 (17): 2173-81; Zer A et al. (2016) J Thoracic. Oncol. 11 (13): 312-23). In advanced colon tumors, the presence of native KRAS is a predictor of clinical benefit of treatment with the EGFR-specific mAbs panitumumab and cetuximab. Additionally, the use of nimotuzumab (another anti-EGFR) combined with gencitabine provides clinical benefit in patients with advanced pancreatic cancer whose tumors are native for KRAS (Schultheis B et al. (2017) Ann. Oncol. 28: 2429-35). However, the use of Cetuximab for the treatment of NSCLC has not shown clinical advantage in any of the subgroups of patients with mutations in the EGFR signaling cascade including, in particular, KRAS. On the other hand, the mutation or not of KRAS in tumors does not influence or condition, by itself, the clinical response of patients to anti-PD1/PDL1 mAbs. In Phase III clinical trials with anti-PD1/PDL1 mAbs in lung cancer, significant clinical benefit was observed for patients with mutated KRAS tumors (Borghaei, H et al. (2015) N Engl J Med. 373 (17): 1627-1639; Socinski May cols. (2018) N Engl J Med. 378 (24): 2288-2301). In agreement with this finding, recent clinical trials show that the presence of other mutations in conjunction with KRAS mutations (co-mutations) could condition a better or worse response in patients treated with anti-PD1/PDL1 mAb. In particular, lung adenocarcinomas in which KRAS co-mutates with the TP53 gene, they lead to immunogenic tumors, more sensitive to CPI. In contrast, the co-mutation in STK11 produces a tumor that is not inflamed and more resistant to this type of therapy (Dong Z Y et al. (2017) Clin Cancer Res 23: 3012-3024; Skoulidis Fy cols. (2018) Cancer Discov; 8: 822-835).

Given the success of EGFR signaling blocking therapies and CPI, several studies have evaluated the benefit of the combined treatment of both approaches in different treatment niches, with varying results. Several authors explored the convenience or not of combining anti-PD1/PDL1 mAbs with TKI therapies that block aberrant signaling by mutated EGFR variants in lung cancer patients. These studies showed no advantage of the combination and significantly increased toxicity (Yang J C et al. (2019) J Thorac Oncol.; 14 (3): 553-9; Schoenfeld A J et al. (2019) Ann Oncol. 30 (5): 839-44). Other authors evaluated the combination with Necitumumab (another anti-EGFR mAb) in lung cancer patients. In this study, the toxicity was manageable, but without evidence of a clinically relevant effect (Besse B et al. (2020) Lung Cancer. 142: 63-69). In none of these trials, an association with the status of the KRAS molecule has been reported.

The present invention reports, for the first time, the use of a therapeutic composition that combines mAbs that block the interaction between PD1 and PDL1 and a vaccine composition that induces Abs against autologous human EGF, in patients with native KRAS. The results obtained show that the therapy is well tolerated and specifically benefits patients with tumors that present native KRAS. Furthermore, this therapy benefits patients with tumors with low PD-L1 expression, which are not very sensitive to anti-PD1/PDL1 mAb therapies.

BRIEF DESCRIPTION OF THE INVENTION

In one embodiment, the present invention relates to the use of therapeutic compositions for the treatment of tumors of epithelial origin. These compositions are characterized by the use of a vaccine composition that induces the production of specific Abs against EGF and a compound that blocks the PD1/PD1 ligand signaling pathway. In particular, the use of the aforementioned therapeutic compositions is described in those tumors of epithelial origin that express the native form of the KRAS protein, preferably those that have the sequences described in SEQ ID NO.: 1 and SEQ ID NO.: 2.

In particular, vaccine compositions that induce the production of Abs against EGF comprise as an active principle a conjugate between recombinant human EGF and a carrier protein. Said carrier protein is selected from the group comprising: cholera toxin B, tetanus toxoid, KLH and *Neisseria meningitidis* p64k protein.

Additionally, the vaccine compositions that induce the production of Abs against EGF have an adjuvant that is selected from the group that comprises: incomplete Freund's adjuvant, based on squalene, of synthetic origin, of mineral origin, of vegetable origin, of animal origin, particulated proteins and liposomes.

The compound that blocks the PD1/PD1 ligand signaling pathway is selected from the group that comprises an anti-PD1 Ab among which are nivolumab, pembrolizumab, MEDI0608 and pidilizumab and an anti-PDL1 Ab which can be: atezolizumab, durvalumab, avelumab, and MDX-1105.

In one embodiment of the present invention, patients are screened by the presence or absence of native KRAS in a sample of their tumor cells. Those with the presence of native KRAS are selected for treatment. Among the types of tumor that are treated are: non-small cell lung cancer, squamous cell head and neck cancer, urothelial carcinoma, colorectal cancer, gastric cancer, esophagus cancer, cervical cancer, hepatocellular carcinoma, Merkel cell carcinoma, renal cell carcinoma, endometrial carcinoma, breast cancer and skin cancer.

In an additional embodiment, the present invention relates to a method for stratifying patients into responders or non-responders to treatment with the therapeutic compositions described herein. The patients are stratified by determining the presence or absence of native KRAS in a sample of the tumor cells and those in whom the presence of native KRAS is detected will be considered responders to treatment. Preferably, those patients whom their tumor samples have PDL1 levels below 1% will be considered responders.

DETAILED DESCRIPTION OF THE INVENTION

KRAS

The methods and uses of the present invention are envisaged for treatment and/or stratification of patients whose epithelial tumors express a wild-type protein KRAS. The term "wild-type" KRAS refers to the naturally occurring KRAS isoforms (Uniprot Acc. No. P01116, version 246 of Apr. 7, 2021). It is envisaged that wild-type KRAS comprises a sequence corresponding to SEQ ID NO.: 1 or SEQ ID No. 2. Particularly, the wild-type KRAS may consist of a sequence corresponding to SEQ ID NO.: 1 or SEQ ID No. 2.

The term "wild-type KRAS" generally also encompasses KRAS polypeptides having mutations relative to the reference sequence shown in SEQ ID NO: 1 (KRAS4A) or SEQ ID No. 2 (KRAS4B) and also encompasses polypeptides having an amino acid sequence which shares as a certain degree of identity with the amino acid sequence shown in SEQ ID NO: 1 (KRAS4A, Uniprot Acc. No. P01116-1) or SEQ ID No. 2 (KRAS4B, Uniprot Acc. No. P01116-2) as described herein. More specifically, "wild-type KRAS" includes KRAS polypeptides having at least 80%, 85%, 90%, 95% or 100% identity with SEQ ID NO.: 1 (KRAS4A) or SEQ ID No. 2 (KRAS4B). In particular, KRAS isoforms 4A and 4B are encompassed by the term "wild-type KRAS". Preferably, the "wild-type KRAS" does not comprise a mutation in its amino acid sequence compared to SEQ ID No. 1 or SEQ ID No. 2, respectively.

Theraputic Composition

The present invention relates to therapeutic compositions for the treatment of cancer aimed particularly at blocking the target EGF and the signaling pathway PD1/PD1 ligand. The present invention describes the effective use of the combination of compounds against PD1 or its ligand PDL1, with agents that reduce concentrations of EGF; in a subpopulation of patients with tumors of epithelial origin, especially those tumors that typically respond to immunotherapy.

Among the compounds against PD1 or its ligand are the MAbs anti-PD1 that are used in the present invention. Such compounds are all those that bind specifically to the cell surface receptor PD1 and block the inhibitory pathway PD1/PDL1. Among these anti-PD1 MAbs are: nivolumab described in U.S. Pat. No. 8,008,449), pembrolizumab described in U.S. Pat. Nos. 8,354,509 and 8,900,587, MEDI0608 (U.S. Pat. No. 8,609,089), pidilizumab (U.S. Pat. No. 8,686,119) and cemiplimab.

The anti-PDL1 MAbs that are used in the present invention are all those that bind specifically to PDL1 and block the inhibitory pathway PD1/PDL1. Among these anti-PDL1 MAbs are: atezolizumab described in U.S. Pat. No. 8,217, 149, durvalumab (U.S. Pat. No. 8,779,108), avelumab described in U.S. Pat. No. 9,624,298 and MDX-1105 (U.S. Pat. No. 7,943,743). Additionally, low molecular weight inhibitors that suppress the interaction PD1/PDL1 can be combined with agents that reduce EGF concentrations, according to the present invention. Among these inhibitors are: BMS1166, BMS202 and CA-170.

The agents that reduce the concentrations of EGF provided in the present invention are all those vaccine compositions that induce the production of specific Abs against the autologous human EGF. Such Abs block the interaction of EGF with the EGF receptor, which contribute to decrease and/or eliminate the levels of serum EGF. Examples of these vaccine compositions are all those that comprise as an active ingredient a conjugate between recombinant human EGF (EGFhr) and a transporter protein. This transport protein could be: cholera toxin B, tetanus toxoid, KLH and P64k from *Neisseria meningitidis*, without being restricted to these. Additionally, these vaccine compositions include an adjuvant that is selected from the following: Freund's incomplete adjuvant, squalene-based adjuvants, synthetic origin, mineral origin, plant origin, animal origin, particulate protein adjuvants and liposomes.

Methods of Identification and/or Selection of Patients

Whether or not a certain patient belongs to the population of patients to be treated by the inventive method can be assessed using routine experimentation known in the art. E.g., in order to determine whether or not an epithelial tumor expresses wild-type KRAS, a tumor sample is typically obtained from the patient to be evaluated, and KRAS nucleic acid sequence is, respectively, obtained from the sample and amplified, and subjected to sequencing. Alternatively, the polymerase chain reaction can detect the presence of KRAS gene.

Another method is related to plasma or serum samples wherein circulating tumor cells with KRAS oncogene can be detected using membrane microarrays. In this regards a positive KRAS mutation in plasma or serum suggests a KRAS mutation in the tumor whereas the absence of a KRAS mutation in the plasma or serum does not necessarily prove a lack of a similar mutation in the pancreatic tumor tissue.

Additionally, or alternatively, expression of wild-type KRAS, can be determined by detecting mutant and/or wild-type KRAS polypeptides in the tumor sample, e.g. by using specific antibodies binding to epitopes specific for wild-type or mutant KRAS, respectively. It is envisaged that patients with epithelial tumors expressing wild-type KRAS are selected for treatment, whereas patients expression mutant KRAS are not selected for treatment.

It is thought that patients with epithelial tumors expressing mutant KRAS and in particular KRAS having on or more mutations as set out elsewhere herein, are less responsive or non-responsive to treatment with the therapeutic compositions used in the methods of the invention. Thus, the present invention also provides a method for stratification of epithelial tumors bearing patients. "Stratification", when used herein, means sorting patients having epithelial tumors into those who may benefit from treatment with therapeutic compositions of the present invention, and those who may not benefit. It is envisaged that patients whose epithelial tumors do not express wild-type KRAS, and in particular patients whose epithelial tumors express mutated KRAS, are not likely to benefit from (be responsive to) treatment with therapeutic compositions herein described.

Otherwise, patients whose PDAC tumors express wild-type KRAS, HRAS or NRAS as defined elsewhere herein are likely to benefit (be responsive to) from the treatment as described herein. Said "wild-type" KRAS preferably has a sequence corresponding to SEQ ID No. 1 or SEQ ID No. 2.

The term "being responsive" in the context of the method of treatment provided herein means that a patient, or tumor, shows a complete response, a partial response or a disease stabilization after administering therapeutic compositions as defined herein, according to Response Evaluation Criteria in Clinical Trials (iRECIST). The term "non-responsive" as used herein means that a patient or tumor shows stable disease or progressive disease after administering the therapeutic compositions as defined herein, according to iRE-CIST. iRECIST is described in Seymour L y cols. RECIST working group (2017) Lancet Oncol. 18(3):e143-e152

Also provided herein is therefore a method of selecting a patient or the population of patients to be treated. This is achieved by determining the presence or absence of mutant and/or wild-type KRAS, in a epithelial tumor sample of each patient. Patients, in whose tumor samples mutant KRAS is detected and/or wild-type KRAS is not detected, are not considered eligible for treatment, whereas patients in whose tumor samples wild-type KRAS is detected and/or mutant KRAS is not detected are considered eligible are therefore selected for treatment in accordance with the invention.

Further, as described before, the invention allows provides a method for prognosis of whether a patient suffering from PDAC, or an epithelial tumor, will be responsive or nonresponsive to treatment with the therapeutic compositions as described herein. As set out before, absence or presence of mutated and/or wild-type KRAS in a tumor sample of the patient can be assessed using routine methods known in the art and described elsewhere herein. Expression of mutated KRAS in the epithelial tumor indicates that the patient, or epithelial tumor, will be nonresponsive to treatment, whereas expression of wild-type KRAS in the epithelial tumor indicates that the patient will be responsive to treatment with the therapeutic compositions as described herein.

In an additional preferred embodiment of the invention, patients responding to treatment will be those expressing native KRAS and in turn, PDL1 levels below 1% measured by immunohistochemical techniques in tumor samples.

Treatment Methods

Among the types of cancer that can be treated with the therapeutic composition described herein are without being limited to: NSCLC, squamous cell cancer of the head and neck, urothelial carcinoma, colorectal cancer, gastric cancer, esophageal cancer, cervical cancer, hepatocellular carcinoma, Merkel cell carcinoma, renal cell carcinoma, endometrial carcinoma, breast cancer, squamous skin carcinoma. In addition, the invention includes refractory or recurrent neoplasms whose growth can be inhibited using the combination of the invention.

The administration of the vaccine compositions comprising EGF as an active ingredient will preferably be carried out intramuscularly; the first four doses every 14 days and the rest, every 28 days, with a permissible time range of 3 days. The dose range in which these compositions will be used will comprise between 20-70 µL/kg of weight or 20-70 µg of total proteins per kilogram of weight or up to 5 mg of total proteins, being more recommended 30-60 µg/kg. The treatment stage will have a minimum duration of 6 months, followed by a maintenance stage that can vary in frequency and dose according to the results obtained. This maintenance period can be optimized taking into account the Abs titer generated and the improvement and/or stabilization of clinical symptoms, provided that a reduction in serum EGF concentrations is guaranteed. Such serum EGF concentrations can be measured by any of the diagnostic sets commercially available for this purpose Anti-PD1 and anti-PDL1 MAbs will be administered at the recommended doses and schedules for each case. In the case of anti-PD1 MAbs will be administered in a dose range between 100-500 mg of total protein intravenously with a frequency of two to six weeks. Anti-PDL1 MAbs will be administered intravenously in a range of 600-1800 mg of total proteins with a frequency of two to five weeks. The administration of the vaccine and MAbs will be adjusted to coincide with the action of blocking PD1/PD1L signaling and inhibition of EGF-mediated signaling. Following this principle, the administration can be concomitant or sequential. In particular, the administration of the vaccine composition may overlap with the administration schemes of the MAbs.

The present invention is further elaborated with the following examples and drawings. However, these examples should not be interpreted as a limitation of the scope of the invention.

EXAMPLES

Example 1. The Combined Administration of CIMAvax-EGF and the Anti-PD1 mAb Nivolumab is Safe and Induces a Potent Anti-Human EGF Abs Response In a phase I/II clinical trial, at the Roswell Park Comprehensive Cancer Center, Buffalo, New York (NCT02955290), a therapeutic composition comprising the vaccine composition CIMAvax-EGF, with the anti-PD1 mAb Nivolumab, was used to the treatment of advanced NSCLC patients.

This study had a Phase I dose escalation and a Phase II efficacy evaluation. In total, 29 patients with metastatic NSCLC were included. Nivolumab was used at a dose of 240 mg every 2 weeks, intravenously. The CIMAvax-EGF vaccine composition was used at a dose of 2.4 mg intramuscularly every 2 weeks during the induction phase (4 doses), followed by monthly injections in the maintenance phase. The first 6 patients received half the dose of CIMAvax-EGF (1.2 mg).

Figure 1:
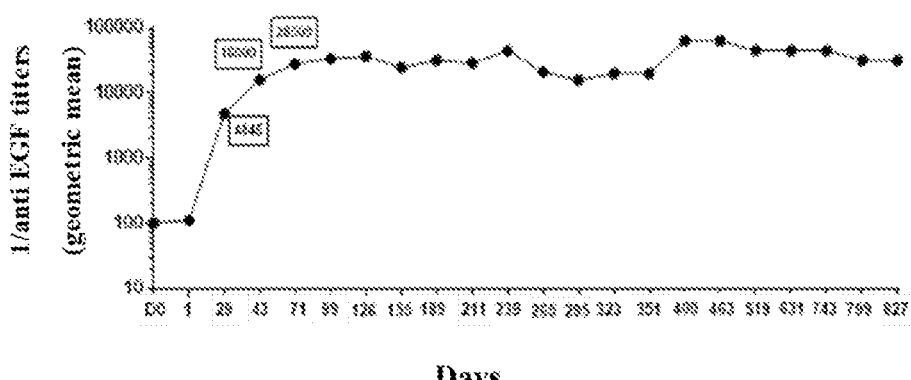
FIG. 1. Anti-EGF Ab titer in serum of patients treated with CIMAvax-EGF and Nivolumab mAb.

The safety profile was favorable and there were no serious adverse reactions related to the applied therapy. CIMAvax-EGF induced a good response in all patients, defined by an anti-EGF Ab titer equal to or greater than 1:4000 (serum dilution (FIG. 1).

A rapid reduction of the EGF concentration in the serum of the patients, measured by ELISA (Human EGF Quan-

Figure 2:
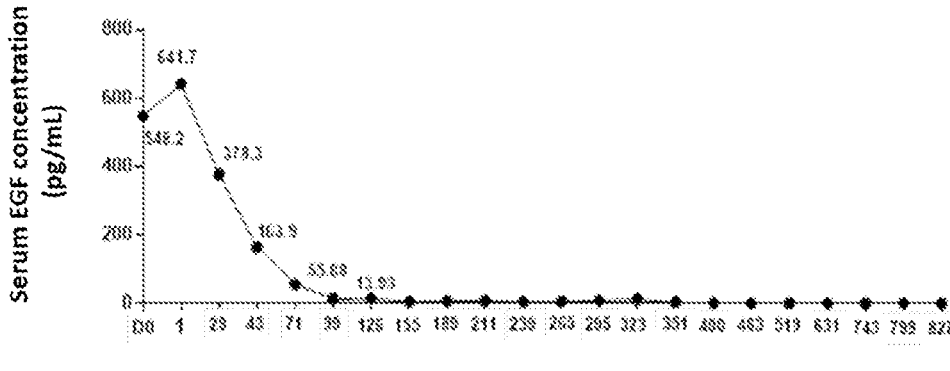
FIG. 2. EGF levels in the serum of patients treated with CIMAvax-EGF and the mAb Nivolumab.

8 tikine ELISA Kit, R&D Systems), was also observed in patients treated with CIMAvax-EGF and mAb nivolumab (FIG. 2).

The median overall survival for the 29 patients treated was 10.36 months. The overall survival rate at one year was 44%.

Figure 3:
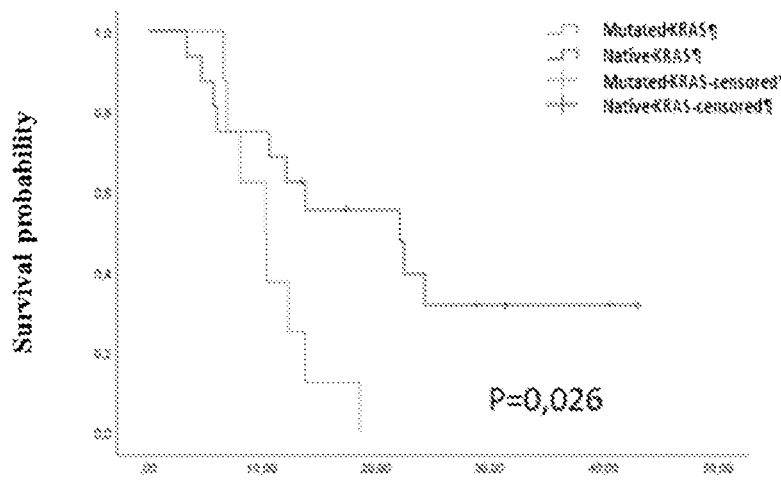
FIG. 3. Cumulative survival of patients treated with CIMAvax-EGF and Nivolumab over time, in patients with native KRAS and mutated KRAS tumors.

Example 2. The Combined Administration of CIMAvax-EGF and the Anti-PD1 mAb Nivolumab Significantly Benefits Native KRAS Patients In the trial described in Example 1, an analysis was carried out by stratifying the patients, according to the presence or not of mutations in the KRAS gene in the tumor. The presence or absence of mutations and the number of copies of the KRAS gene was verified using a new generation sequencing assay that uses multiparametric PCR-based DNA sequencing. Surprisingly, the survival of patients with native KRAS was significantly higher than that of patients with mutated KRAS (FIG. 3).

Median survival was 22.06 months in native KRAS patients and 10.26 months in mutated KRAS patients. The one-year survival rate was 69% in the native KRAS patients and 37% in the mutated KRAS patients.

Additionally, after combination therapy, patients with native KRAS had a significant improvement in the disease control rate (patients with at least stabilization of the disease according to irRECIST criteria (Seymour L et al. RECIST working group (2017) Lancet Oncol. 18 (3): e143-e152). In patients with native KRAS, the disease control rate after the combination of CIMAvax-EGF and Nivolumab was 56.3% compared to 12.5% in patients with tumors containing KRAS mutations.

The survival observed with the combined therapy in patients with native KRAS is clinically relevant since, according to the literature, stratification according to KRAS mutations does not influence the survival of patients treated only with Nivolumab mAb. In these patients with advanced NSCLC, monotherapy with Nivolumab resulted in a median survival of 11.2 months and 10 months, in patients with mutated or native KRAS, respectively (Passiglia F et al. (2019) Br J Cancer 120 (1): 57-62).

Example 3. The Combined Administration of CIMAvax-EGF and the Anti-PD1 Ab Nivolumab Significantly Benefits Patients with Native KRAS Tumors and PDL1<1%

Figure 4:
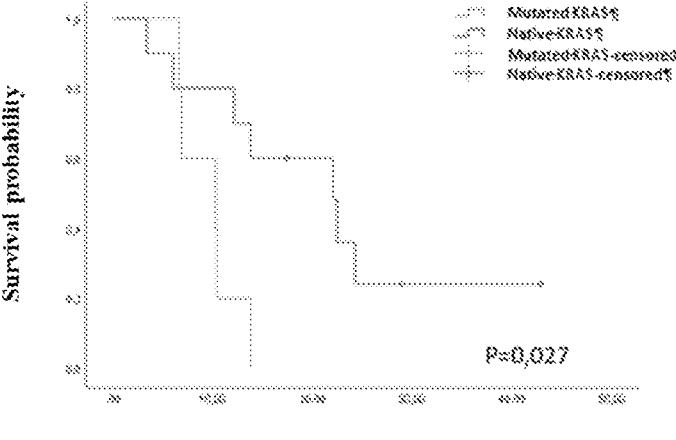
FIG. 4. Cumulative survival of patients treated with CIMAvax-EGF and Nivolumab over time, for patients with PD-L1 tumors <1%, which are native KRAS or mutated KRAS.

Given the known history in the literature of a lower response to monotherapy with anti-PD1 mAb in patients with low expression of PDL1 in the tumor, the analysis of example 2 was repeated for patients whose tumors did not express PDL1 (PDL1<1%). PDL1 expression was determined using pharmDx assay 28-8 for PDL1 determination. Surprisingly, it was observed that the stratification of the patients according to the mutations in KRAS again differentiated the survival of the patients. Median survival was 22.06 months in native KRAS patients and 10.26 months in mutated KRAS patients. The one-year survival rate was very high, 80% in patients with native KRAS (FIG. 4).

The invention claimed is:

1. A method of treating a tumor of epithelial origin in a patient, comprising administering to the patient i) a vaccine composition that induces the production of specific antibodies (Ab) against epidermal growth factor (EGF) and ii) a compound that blocks PD1/PD1 ligand (PD-L1) signaling pathway, wherein the patient is selected for treatment by determining the presence of human KRAS protein in a sample of the patient's tumoral cells and the human KRAS protein has an amino acid sequence selected from the group consisting of SEQ ID NO: 1 and SEQ ID NO: 2.

2. The method of claim 1, wherein the vaccine composition that induces the Ab production against the EGF comprises a conjugate between human recombinant EGF and a carrier protein.

3. The method of claim 2, wherein the carrier protein is selected from the group consisting of:
cholera toxin B subunit,
tetanus toxoid,
KLH and
P64k of Neisseria meningitidis.

4. The method of claim 3, wherein the vaccine composition additionally comprises an adjuvant selected from the group consisting of:
incomplete Freund's adjuvants,
squalene-based adjuvants,
synthetic origin adjuvants,
mineral origin adjuvants,
vegetable origin adjuvants,
animal origin adjuvants,
particulated proteic adjuvants and
liposomes.

5. The method of claim 1, wherein the compound that blocks PD1/PD-L1 signaling pathway is selected from the group consisting of:
an anti-PD1 Ab and
an anti-PD-L1 Ab.

6. The method of claim 5, wherein the anti-PD1 Ab is selected from the group consisting of: nivolumab, pembrolizumab, cemiplimab, MEDI0608 and pidilizumab.

7. The method of claim 5, wherein the anti-PD-L1 Ab is selected from the group consisting of: atezolizumab, durvalumab, avelumab and MDX-1105.

8. The method of claim 1, wherein the tumor of epithelial origin is selected from the group consisting of: non-small cell lung cancer, squamous cell head and neck cancer, urothelial carcinoma, colorectal cancer, gastric cancer, esophagus cancer, cervical cancer, hepatocellular carcinoma, Merkel cell carcinoma, renal cell carcinoma, endometrial carcinoma, breast cancer and skin cancer.

9. A method of treating a tumor of epithelial origin in a patient comprising: administering a therapeutic regimen to the patient, wherein the therapeutic regimen comprises i) a compound that blocks epidermal growth factor (EGF) and ii) an antibody (Ab) that blocks PD1/PD-L1 signaling pathway, wherein the patient is selected for treatment by determining the presence of human KRAS protein in a sample of the patient's tumoral cells and the human KRAS protein has an amino acid sequence selected from the group consisting of SEQ ID NO: 1 and SEQ ID NO: 2.

10. The method of claim 9, wherein less than 1% of the tumoral cells express PD-L1.

11. The method of claim 9, wherein the tumor of epithelial origin is selected from the group consisting of: non-small cell lung cancer, squamous cell head and neck cancer, urothelial carcinoma, colorectal cancer, gastric cancer, esophagus cancer, cervical cancer, hepatocellular carcinoma, Merkel cell carcinoma, renal cell carcinoma, endometrial carcinoma, breast cancer and skin cancer.

12. The method of claim 1, wherein the tumor of epithelial origin is non-small cell lung cancer.

13. The method of claim 9, wherein the tumor of epithelial origin is non-small cell lung cancer.

14. The method of claim 1, the tumor of epithelial origin comprises the human KRAS protein.

15. The method of claim 9, wherein the tumor of epithelial origin comprises the human KRAS protein.

16. A method of treating a tumor of epithelial origin in a patient, comprising:
(a) determining that the tumor of epithelial origin comprises human KRAS protein having an amino acid sequence selected from the group consisting of SEQ ID NO: 1 and SEQ ID NO: 2, and
(b) administering to the patient i) a vaccine composition that induces the production of specific antibodies (Ab) against epidermal growth factor (EGF) and ii) a compound that blocks PD1/PD1 ligand (PD-L1) signaling pathway.

17. The method of claim 16, wherein the tumor of epithelial origin is selected from the group consisting of: non-small cell lung cancer, squamous cell head and neck cancer, urothelial carcinoma, colorectal cancer, gastric cancer, esophagus cancer, cervical cancer, hepatocellular carcinoma, Merkel cell carcinoma, renal cell carcinoma, endometrial carcinoma, breast cancer and skin cancer.

18. The method of claim 16, wherein the tumor of epithelial origin is non-small cell lung cancer.

19. The method of claim 16, wherein the compound that blocks PD1/PD-L1 signaling pathway is selected from the group consisting of:
an anti-PD1 Ab and
an anti-PD-L1 Ab.

20. The method of claim 19, wherein the anti-PD1 Ab is selected from the group consisting of: nivolumab, pembrolizumab, cemiplimab, MEDI0608 and pidilizumab.

* * * * *